United States Patent [19]

Fisher

[11] Patent Number: 4,618,462

[45] Date of Patent: Oct. 21, 1986

[54] HUMIDIFIER WITH CONTROLLED HEAT INPUT

[76] Inventor: Robert S. Fisher, 2 Haite Close, West Pymble, New South Wales, 2073, Australia

[21] Appl. No.: 663,073

[22] Filed: Oct. 17, 1984

[30] Foreign Application Priority Data

Oct. 24, 1983 [AU] Australia ............................. PG2001

[51] Int. Cl.$^4$ ................................................ B01F 3/04
[52] U.S. Cl. .................................... 261/130; 219/272; 219/274; 236/44 C; 261/104; 261/122; 261/131; 261/142; 261/147; 261/154; 261/DIG. 65
[58] Field of Search ............... 261/122, 129, 130, 142, 261/146, 147, 154, 104, 107, 131, DIG. 65; 236/44 R, 44 C; 219/271-276; 128/203.27, 204.13

[56] References Cited

U.S. PATENT DOCUMENTS

| | | | |
|---|---|---|---|
| 435,856 | 9/1890 | Parker | 261/147 X |
| 528,882 | 11/1894 | Keller | 261/154 X |
| 3,659,604 | 5/1972 | Melville et al. | 261/DIG. 65 |
| 3,954,920 | 5/1976 | Heath | 261/DIG. 65 |
| 3,982,095 | 9/1976 | Robinson | 261/122 X |
| 4,051,205 | 9/1977 | Grant | 261/DIG. 65 |
| 4,225,542 | 9/1980 | Wall et al. | 261/DIG. 65 |
| 4,419,302 | 12/1983 | Nishino et al. | 261/DIG. 65 |
| 4,436,674 | 3/1984 | McMenamin | 261/DIG. 65 |

FOREIGN PATENT DOCUMENTS 1242694  8/1971  United Kingdom .
1301582  12/1972  United Kingdom .

OTHER PUBLICATIONS

"The Freezing of Supercooled Water in Glass", by R. G. Wylie, CSIRO, Nat'l Standards Lab., N.S.W. Austr., 1952, pp. 244, 245 (10/17/52).
"Enhancement of Water Vaper, etc.", by R. W. Hyland & A. Wexler–Journal of Research of National Bureau of Standards—A. Phys. & Chem.—vol. 77A, #1, '73.
"Accurate Determination of Mol. Interaction in Gas—Vapour Mixture", by R. G. Wylie & R. S. Fisher—CSIRO Div. of Physics, N.S.L. Sydney (about 1974).
Encyclopaedic Dictionary of Physics—Pergamon Press, Oxford, Pergamon, 1961, p. 723.
Journal of Research of National Bureau of Standards—A. Physics and Chemistry, vol. 81A, No. 1–Jan. Feb. 1977—pp. 82–84.
Journal of Chemistry and Physics (sometime in 1984) "The Molecular Interaction of Water Vapour and Air", by Russel G. Wylie & R. S. Fisher.

Primary Examiner—Richard L. Chiesa
Attorney, Agent, or Firm—Nies, Webner, Kurz & Bergert

[57] ABSTRACT

The present invention relates to humidifiers as used in research and in the calibration of humidity measuring instruments for producing a saturated gas stream. Specifically the invention relates to humidifiers comprising a bubble type and an extended surface type humidifier in gas flow communication one to the other and including temperature control means.

8 Claims, 1 Drawing Figure

HUMIDIFIER WITH CONTROLLED HEAT INPUT

BACKGROUND OF THE INVENTION

1. Field of the Invention

The present invention relates to a humidifier able to accurately produce a humidified gas stream.

Accurately controlled humidities are required for many applications, particularly in research on the effects of humidity on a wide variety of things and for the calibration of humidity measuring instruments. For some methods of producing accurately known humidities a means of humidifying a gas stream precisely to the point of saturation at a known temperature is required.

In theory, a gas stream in close contact with and flowing across the surface of the liquid with which it is being humidified at constant temperature, approaches asymptotically to the point of saturation (the point of equilibrium where no more vapour can be accepted by the gas). In theory, if the geometry, flow rate and dimensions are suitably chosen the approach to saturation can be made as close as required.

2. Description of the Prior Art

Prior known devices for producing saturated gas include bubble type humidifiers and extended surface humidifiers.

Bubble type humidifiers operate by passing the gas in fine bubble form through the liquid. Such devices whilst being able to produce large quantities of saturated gas suffer two major disabilities. Firstly, as the gas bubbles pass through the liquid gas interface fine liquid particles become entrained in the gas, and secondly as the point of saturation is gas temperature dependent, it is difficult to obtain precision as the gas temperature is not directly controlled.

Extended surface type humidifiers including liquid surface or wick type humidifiers are not well adapted to produce large quantities of saturated gas.

It is an object of the present invention to overcome or at least ameliorate the above-mentioned shortcomings of the prior art.

In the present invention a bubble humidifier and an extended surface humidifier are combined to form an efficient and accurate saturating humidifier A primary bubble humidifier comprises a vessel containing the liquid, usually but not necessarily water, through which the air or other gas to be humidified is bubbled. The gas is then passed to a secondary extended surface humidifier comprising a labyrinth of wicking fully wetted with the liquid. The bubble humidifier is able to produce a gas stream close to the saturation point in a small space with simple equipment but may be inaccurate by having insufficient liquid depth and by producing aerosol spray in the gas stream.

The labyrinth form of extended surface humidifier is very effective at removing spray, and since the gas is already approximately saturated, the labyrinth may be small, as it does not require very high capacity.

A feature of the present invention is the provision of a means for providing a controlled amount of power to balance the latent heat of evaporation of the liquid in the bubble humidifier as a gas stream is humidified.

The amount of energy required is determined by a feedback controller which senses the temperature at a suitable point on or in the humidifier, compares this temperature with the required reference value and thereby derives an error signal which after suitable processing provides a power input to the humidifier to reduce the temperature error to zero or make it negligibly small.

The principle of providing controlled power to balance the power consumed as latent heat of evaporation to maintain the correct gas stream temperature may be extended to the labyrinth humidifier.

SUMMARY OF THE INVENTION

The present invention consists in a humidifier for evaporating a liquid into a gas comprising:

a bubble humidifier including a gas inlet and a bubble chamber adapted to be liquid filled;

a labyrinth extended surface humidifier connected for gas flow communication with said bubble humidifier and including a gas outlet;

a first temperature control means for controlling the temperature of liquid in said bubble humidifier, and a second temperature control means for controlling the gas temperature in said labyrinth extended surface humidifier.

In a preferred form of the present invention the labyrinth comprises a roll of laminate comprising a strip of corrugated wire mesh and a strip of absorbent material wherein the corrugated wire is utilised as the heating element for maintaining the labyrinth at a constant temperature

BRIEF DESCRIPTION OF THE DRAWINGS

An embodiment of the present invention will now be described by way of example only with reference to the accompanying drawing in which.

DESCRIPTION OF THE PREFERRED EMBODIMENT

Figure 1:
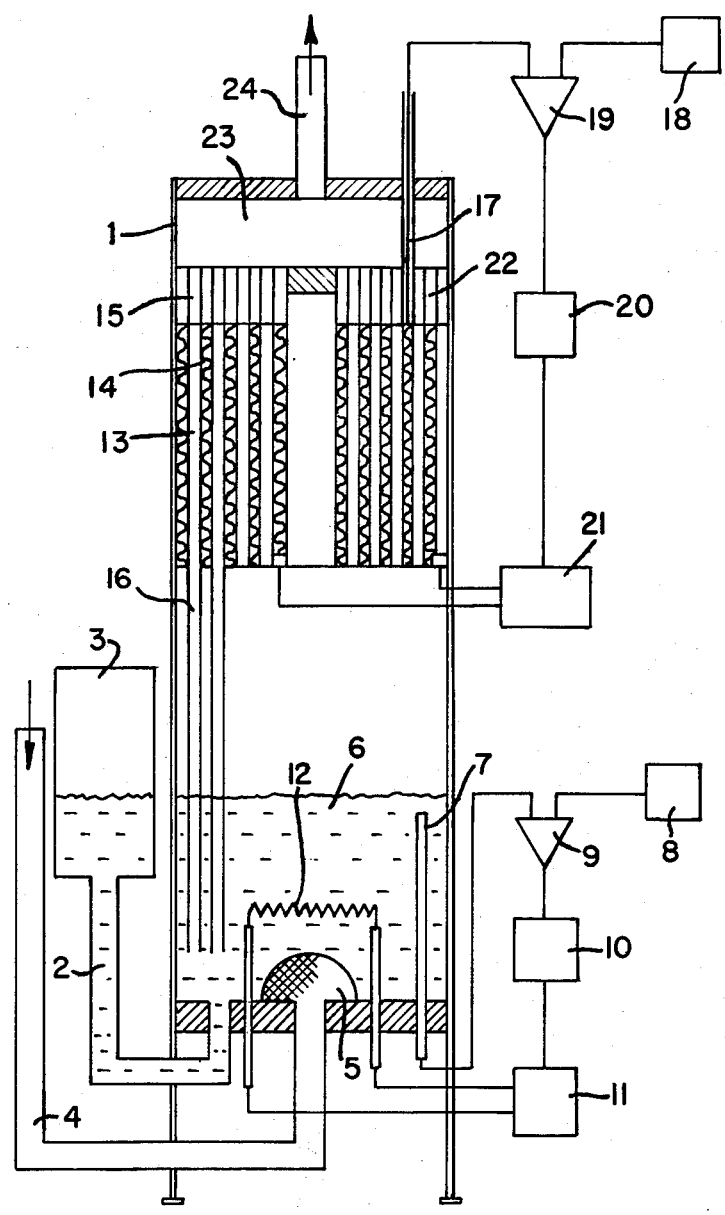
FIG. 1 is a sectional side elevation showing a humidifier according to the invention.

Referring to the drawing, a humidifier comprising a cylindrical vessel containing a temperature controlled bubble humidifier and a temperature controlled extended surface humidifier is shown.

The cylindrical vessel 1 is connected for liquid flow communication to a water reservoir 3 by a water feed pipe 2. A gas supply pipe 4 conducts gas to a porous gas distributer 5 which breaks the gas stream into bubbles in the liquid 6 within the vessel 1. The temperature of the liquid within the bubble humidifier is measured by a thermo-electric sensor 7 producing a primary voltage signal. That signal is compared by a comparator 9 with a reference value from a reference voltage source 8. An error signal from comparator 9 is modified at 10 and controls a power amplifier 11 supplying electrical power to a heater 12 which heats the water 6 to bring it to a predetermined temperature set by the value of the voltage from source 8.

A labyrinth cartridge 13 comprises a strip of corrugated stainless steel mesh 14 rolled together with a strip of absorbent material, in this case filter paper 15. The filter paper strip inlcudes a series of tails 16 (wick elements) which dip into the liquid 6 in the bubble humidifier and transmit it by capillary action to the labyrinth 13.

As mentioned earlier the temperature in the labyrinth 13 is adjusted to bring it to the predetermined temperature by utilizing the stainless steel mesh 14 as a heating element. This has the advantage of enabling a nearly constant temperature to be maintained throughout the labyrinth 13. The heater is controlled by a second thermo-electric sensor 17, a reference voltage source 18 a comparator 19, modifier 20 and power amplifier 21 which operate in a manner as above described for the bubble humidifier.

Gas approximately saturated, coming from the bubble humidifier impinges up on the wet walls of the labyrinth 13 during its circuitous path through the stainless steel mesh 14 to remove any spray droplets. If any evaporation takes place the latent heat absorbed will be re-supplied by the control system which maintains the temperature of the gas within the labyrinth at the predetermined temperature.

The gas after being conditioned in the labyrinth 13 passes through a passive (uncontrolled) section 22 consisting only of the close spaced parallel walls of wetted filter paper extended above the stainless steel mesh 14. From the passive section 22 the gas is collected in a chamber 23 and leaves the vessel 1 through a pipe 24 which conducts the gas to its point of application.

The principles ennunciated in this invention include the accurate supply of heat to a humidifier to compensate for the heat absorbed as latent heat of evaporation, the controlled production of this heat by a feedback or servo-mechanism control, and the application of this heat in a manner which avoids the inaccuracies caused by temperature gradients where the heat is conducted to the evaporating surfaces. It is important that the temperature be measured by the controller at the point where the saturation is completed.

Whilst the invention has been described with reference to a humidifier wherein a bubble humidifier and an extended surface humidifier are combined within a single vessel, it will be appreciated by those skilled in the art that any configuration of the two humidifiers combined to give the improved result will fall within the scope of the present invention.

I claim:

1. A humidifier for evaporating a liquid into a gas comprising:
    a bubble humidifier including a gas inlet and a bubble chamber containing said liquid and connected in gas flow communication with said gas inlet;
    a labyrinth extended surface humidifier positioned in spaced relation above said liquid connected in gas flow communication with said bubble chamber and an extend surface element located throughout said surface humidifier;
    a series of capillary action water transmitting means connecting said liquid in said bubble chamber and said surface element in said surface humidifier;
    a first heat generating means for heating the liquid in said bubble chamber; and
    a first temperature control means responsive to temperature within the bubble chamber for controlling the operation of said first heat generating means.

2. A humidifier according to claim 1, including a second heat generating means for heating the gas in said labyrinth extended surface humidifier and a second temperature control means responsive to temperature within the labyrinth for controlling the operation of said second heat generating means.

3. A humidifier according to claim 2 wherein said labyrinth extended surface humidifier comprises a roll of a laminate, said laminate comprising a strip of wire mesh and superimposed thereon a strip of absorbent material, and said capillary action means dampens said absorbent material.

4. A humidifier according to claim 3 wherein said first temperature control means comprises a temperature sensor producing a first signal indicative of liquid temperature, a means for comparing said first signal with a predetermined value to produce a first error signal, said first heat generating means being responsive to said first error signal to bring said liquid temperature into coincidence with said predetermined value.

5. A humidifier according to claim 4 wherein said second temperature control means comprises a temperature sensor producing a second signal indicative of gas temperature, a means for comparing said second signal with a predetermined value to produce a second error signal, said second heat generating means being responsive to said second error signal to bring said gas temperature into coincidence with said predetermined value.

6. A humidifier according to claim 5 wherein said second heat generating means is said strip of wire mesh.

7. A humidifier according to claim 6 where said strip of wire mesh is corrugated.

8. A humidifier according to claim 7 wherein said said capillary action means for dampening said absorbent material comprises a plurality of wick elements extending between said absorbent material and said bubble chamber.

* * * * *

UNITED STATES PATENT AND TRADEMARK OFFICE
CERTIFICATE OF CORRECTION

PATENT NO. : 4,618,462

DATED : October 21, 1986

INVENTOR(S) : ROBERT S. FISHER

It is certified that error appears in the above-identified patent and that said Letters Patent is hereby corrected as shown below:

Column 4, line 17, change "claim 2" to --claim 1 or 2--.

Signed and Sealed this

Thirtieth Day of December, 1986

Attest:

DONALD J. QUIGG

*Attesting Officer*  *Commissioner of Patents and Trademarks*